United States Patent [19]

Zeitlin et al.

[11] Patent Number: 4,777,287

[45] Date of Patent: Oct. 11, 1988

[54] RECYCLE OF VAPORIZED SOLVENT IN LIQUID PHASE OXIDATION OF AN ALKYL AROMATIC

[75] Inventors: Martin A. Zeitlin, Naperville, Ill.; Stafford J. McQuillin, Mount Pleasant, S.C.

[73] Assignee: Amoco Corporation, Chicago, Ill.

[21] Appl. No.: 665,751

[22] Filed: Oct. 29, 1984

[51] Int. Cl.$^4$ .................................... C07C 51/265
[52] U.S. Cl. .................................. 562/414; 562/413
[58] Field of Search ........................... 562/413, 414

[56] References Cited

U.S. PATENT DOCUMENTS 3,092,658 6/1963 Baldwin et al. ...................... 562/413
3,187,038 6/1965 Hundley ............................. 562/414

OTHER PUBLICATIONS

Perry, R. H. Ed., Chemical Engineers' Handbook, 5th Ed., McGraw-Hill Book Co., New York, 1973, pp. 5-1-5-7.

*Primary Examiner*—Michael L. Shippen
*Attorney, Agent, or Firm*—James R. Henes; William H. Magidson; Ralph C. Medhurst

[57] ABSTRACT

A method is disclosed for the continuous production of an aromatic carboxylic acid by the liquid phase, exothermic oxidation of an alkyl aromatic in a solvent in an oxidation reactor employing an overhead condenser system for condensation and recycle of vaporized solvent to the reactor, wherein the oxidation is performed at a relatively reduced temperature or pressure or at a relatively increased throughput of the alkyl aromatic without exceeding the elevation head between the condenser system and the reactor.

6 Claims, 1 Drawing Sheet

RECYCLE OF VAPORIZED SOLVENT IN LIQUID PHASE OXIDATION OF AN ALKYL AROMATIC

BACKGROUND OF THE INVENTION

1. Field of the Invention

This invention relates generally to the continuous, liquid phase oxidation of an alkyl aromatic with an oxygen-containing gas at an elevated temperature and pressure and in the presence of an oxidation catalyst, and more particularly concerns a method for effecting this known oxidation process either at a relatively reduced temperature or pressure or at a relatively increased throughput of the alkyl aromatic.

2. Description of the Prior Art

The liquid phase oxidation of an alkyl aromatic is a highly exothermic reaction. Conventional processes for the oxidation of alkyl aromatics in the liquid phase to form carboxylic acids are generally performed in vertically disposed cylindrical reactors with a substantial portion of the heat generated by the exothermic oxidation being removed by directly evaporating a portion of the solvent and alkyl aromatic in the reaction mixture. The remainder of the heat generated results in an increase in the temperature of the reaction mixture. The temperature of the reaction mixture is determined principally by the total amount of heat generated in the oxidation less that amount of heat removed by solvent evaporation and, except for variances resulting from imperfect mixing of the reaction mixture within the reactor, the temperature of the reaction mixture is substantially the same throughout the reactor.

Because of the great commercial importance of the oxidation of alkyl aromatics, it is highly desirable to improve the yield and quality of aromatic carboxylic acids produced thereby. It has been discovered that the use of lower process temperatures in this oxidation process affords selectivity and product quality benefits. Lower process temperatures favor the oxidation reaction over competing reactions which lead to the formation of undesirable products which reduce the yield and purity of the aromatic carboxylic acids produced. An increased yield of the aromatic carboxylic acid product could be effected by an increased throughput of the alkyl aromatic feedstock through the oxidation reactor.

On the one hand, at a given throughput of the alkyl aromatic feedstock, everything else being equal, the process temperature could be lowered by reducing the process pressure. In that case, increased vaporization of the reaction solvent would occur at the reduced reaction pressure, and relatively greater amounts of the given amount of heat generated by the exothermic oxidation could be removed by the increased vaporization. On the other hand, everything else being equal, increased throughputs of the alkyl aromatic feedstock could be employed if the increased heat generated thereby could be dissipated by increased vaporization of the reaction solvent at a reduced reaction pressure.

However, a serious obstacle associated with the operation of the overhead condenser system must be overcome before the liquid phase oxidation of the present invention could be operated at a lower process pressure. In particular, the material—that is, solvent and alkyl aromatic—vaporized as a result of the heat generated in the exothermic reaction and unreacted oxygen and other components of the air fed to the reactor pass upward through the reactor and are withdrawn from the reactor from a point above the top level of the liquid reaction mixture in the reactor and passed upward and out of the reactor to an overhead condenser system where the vaporized solvent and alkyl aromatic are condensed for recycle by gravity to the reactor. The non-condensible gases are vented from the condenser through a vent.

The overhead condenser system can be made up of one or more condensers; and, if the overhead condenser system comprises a plurality of condensers, typically they are operated in series. Conventionally, the condensed solvent and alkyl aromatic are recycled through one or more lines from the condenser system to the reactor at a point high in the reactor. However, in such a system, pressure drops which develop in the line through which the vaporized material is conveyed from the reactor to the overhead condenser system and through the overhead condenser system itself limit the pressure available to overcome any back pressure at the point in the reactor where the condensed material is returned to the reactor. Under conditions where the process pressure is reduced, both the rate of vaporization in the reactor and the volumetric flow rate of vaporized solvent and alkyl aromatic from the reactor to the condenser system are increased, thereby increasing the pressure drop therein and further decreasing the pressure available in the line to overcome any back pressure within the reactor. Ultimately a point is reached where the pressure drop through the condenser system exceeds the elevation head, and gravity flow of the condensed solvent and alkyl aromatic from the overhead condenser system to the reactor is not possible. This limitation has prevented the benefits from operation of the aforesaid liquid phase oxidations at lower temperatures and pressures and at higher throughputs of the alkyl aromatic from being attained.

It is known in the prior art to return the condensed material from the overhead condenser system to a point high in the reactor through a line external to the reactor and then through a line inside the reactor through the hot reaction mixture within the reactor to a point low in the reactor where the condensed solvent and alkyl aromatic is finally discharged to the reactor. However, the use of a line inside the reactor to bring the condensed material from a point high in the reactor to a point low in the reactor suffers from several disadvantages. Such an interior line can lead to dead zones within the reaction mixture inside the reactor where inefficient and incomplete mixing may occur, and can also lead to the precipitation of solids on the outer surface of the line which would further reduce the mixing efficiency. In addition, since the condensed materials in the interior line are warmed by heat transferred from the reaction mixture along the entire length of the interior line, the potential cooling power that the condensed materials possess as they enter the reactor is not fully utilized in the primary reaction zone in the bottom portion of the reactor. Instead their cooling power is dissipated to a considerable extent by the less efficient indirect heat transfer through the interior line.

OBJECTS OF THE INVENTION

It is therefore a general object of the present invention to provide an improved method for the continuous, liquid phase oxidation of an alkyl aromatic with oxygen-containing gas in the presence of an oxidation catalyst which meets the aforementioned goals and solves the aforementioned problems.

More particularly, it is an object of the present invention to provide an improved method for effecting the aforesaid known oxidation process to produce an aromatic carboxylic acid with improved selectivity and product quality.

It is a related object of the present invention to provide an improved method for effecting the aforesaid known oxidation process to produce an aromatic carboxylic acid with improved yields.

Other objects and advantages of the invention will become apparent upon reading the following detailed description and appended claims, and upon reference to the accompanying drawing.

SUMMARY OF THE INVENTION

These objects are achieved by an improvement in a method for the continuous production of an aromatic carboxylic acid by the liquid phase, exothermic oxidation of an alkyl aromatic with an oxygen-containing gas in a solvent in an oxidation reactor at an elevated temperature and pressure and in the presence of an oxidation catalyst, wherein heat generated in the oxidation reactor is at least partially dissipated by vaporization of the solvent therein, the vaporized solvent is withdrawn from the top of the oxidation reactor and condensed in an overhead condenser system and the condensed solvent is recycled by gravity flow to the oxidation reactor. The improvement comprises recycling at least a portion of the condensed solvent from the overhead condenser system to the bottom portion of the oxidation reactor through a line exterior to the oxidation reactor, to maximize the available pressure head between the overhead condenser system and the point in the reactor to which the aforesaid portion of the condensed solvent is recycled.

BRIEF DESCRIPTION OF THE DRAWINGS

For a more complete understanding of this invention, reference should now be made to the embodiment illustrated in greater detail in the accompanying drawing and described below by way of examples of the invention.

Figure 1:
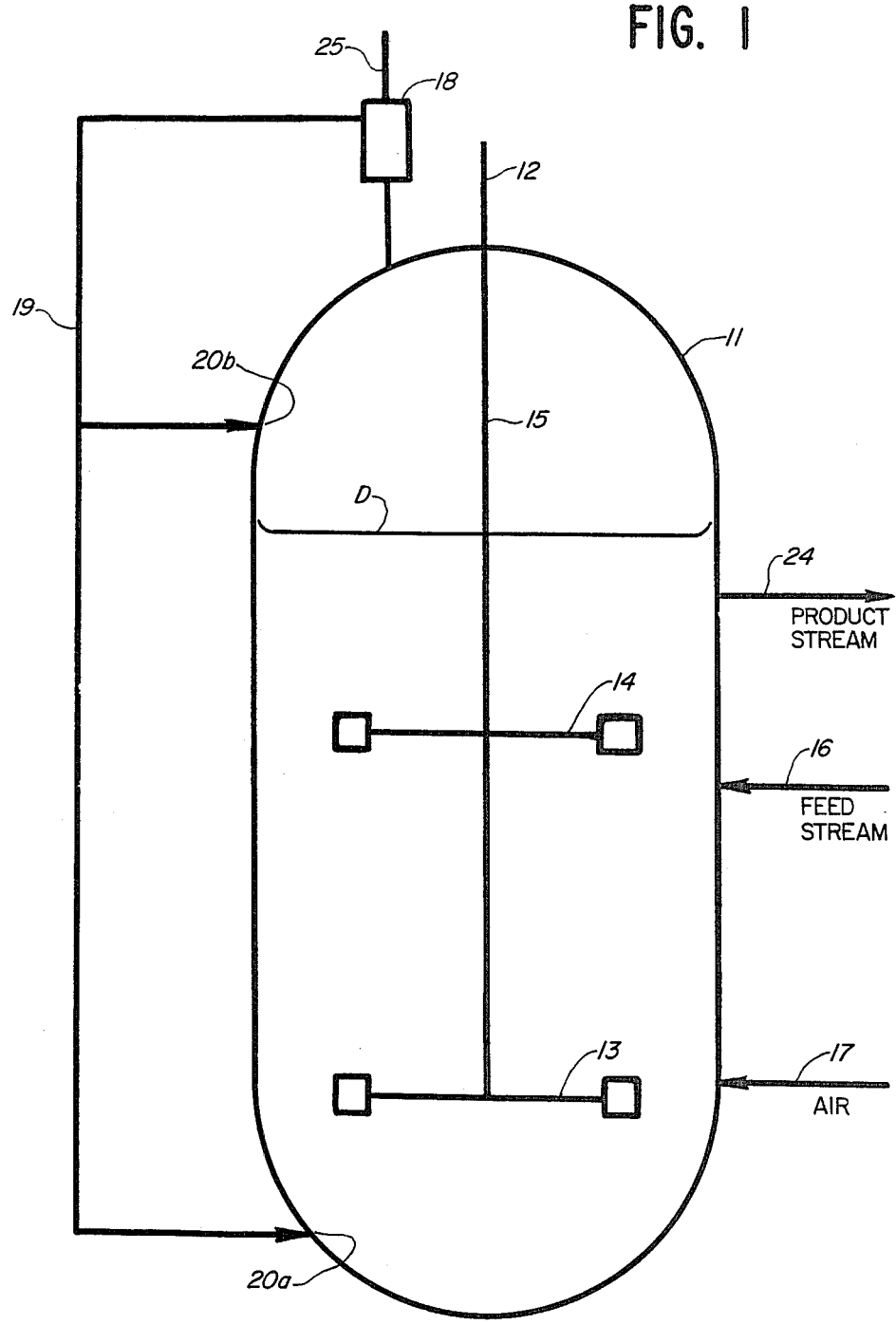
FIG. 1 is a schematic illustration of a reactor for the liquid phase oxidation of an alkyl aromatic in a solvent to form an aromatic carboxylic acid wherein a portion of the solvent and alkyl aromatic vaporized in the reactor and condensed in an overhead condenser system is recycled to the bottom of the reactor.

It should be understood that the drawing is a schematic illustration and that in certain instances, details which are not necessary for an understanding of the present invention or which render other details difficult to perceive may have been omitted. It should be understood of course that the invention is not necessarily limited to the particular embodiments illustrated herein.

DETAILED DESCRIPTION OF THE DRAWING INCLUDING PREFERRED EMBODIMENTS

The aforedescribed obstacle to operating the liquid phase oxidation of an alkyl aromatic to an aromatic carboxylic acid at a lower process temperature, a lower process pressure and/or at a higher throughput of the alkyl aromatic, is overcome in the method of the present invention by recycling at least a portion of the condensed solvent and alkyl aromatic from the overhead condenser system to a point at or near the bottom of the oxidation reactor, in contrast to recycling all of the condensed solvent and alkyl aromatic to the reactor at a point near the top of the reactor as has been done conventionally in the prior art. Recycling at least a portion of the condensed material to the reactor at a point at or near the bottom of the reactor maximizes the pressure head which exists between the condenser and the point in the reactor to which the aforesaid portion of the condensed material is recycled and which is available to overcome the back pressure within the reactor at that point. This therefore permits performance of the liquid phase oxidation at lower process pressures and with the resulting higher rates of vaporization in the reactor and higher pressure drops in the line in which the vaporized material is passed from the reactor to the condenser system as a result of the increased volumetric flow rates therein. Thus, relative to recycling all of the condensed material to a point high in the oxidation reactor, recycling at least a portion of the condensed material to a point low in the oxidation reactor permits substantially increased flexibility in regard to using relatively lower process pressures and hence permits the product quality and yield benefits accruing from the use of reduced process temperatures and pressures and of increased alkyl aromatic throughputs to be attained.

Furthermore, as indicated hereinabove, recycle of at least a portion of the condensed solvent and alkyl aromatic to a point low in the oxidation reactor through a line external to the reactor affords the additional benefits of maximizing the potential cooling effect of the aforesaid portion of the condensed materials by direct heat exchange between the condensed materials and reactor contents in the primary reaction zone at the bottom of the reactor without dissipating the potential cooling power of the aforesaid portion through less efficient indirect heat exchange along the full length of a line inside the reactor and extending from the top region to the bottom region of the reactor. Furthermore, by contrast to the use of an internal line, the use of an exterior line to recycle condensed materials to the bottom of the reactor avoids complicating the reactor internals, the creation of dead zones in the reaction mixture where inefficient and incomplete mixing can result, and the precipitation of solids on the outer surface of the line which would further reduce the mixing efficiency.

Turning first to FIG. 1, there is shown a schematic illustration of a preferred embodiment of the method of this invention. A reactor 11 is maintained under sufficient elevated pressure to maintain the solvent and alkyl aromatic substantially in the liquid state and is equipped with an agitator 12 comprising impellers 13 and 14 which are rotated in a horizontal plane in the reactor 11 by means of central shaft 15. A feed stream comprising the entire supply of the alkyl aromatic and catalyst to the reactor 11, both dissolved in a portion of the total amount of solvent introduced into the reactor 11, is introduced through inlet pipe 16 into the reactor 11. Air is introduced through inlet pipe 17 into the reactor 11. Recycle solvent and alkyl aromatic from the condenser system 18 are recycled through inlet pipe 19 into the reactor 11. The recycle solvent flows into the reactor 11 from inlet pipe 19 through the outlets 20a and 20b. The portion of the condensed solvent and alkyl aromatic recycled through the outlet 20a is introduced into the reactor at a point at or near the bottom thereof. Of the total amount of condensed solvent and alkyl aromatic that is recycled from the condenser system 18 to the reactor 11, the percentage that is recycled to a point in the reactor 11 at or near the bottom thereof is preferably at least 5 percent, more preferably at least 10 percent, and most preferably at least 50 percent. Ideally essentially all of the condensed solvent and alkyl aromatic is recycled to the bottom of the reactor 11.

The alkyl aromatic, oxidation catalyst and solvent in the feed stream combine with the air and recycle solvent in the reactor 11, wherein at least a portion of the alkyl aromatic is oxidized by oxygen in the presence of the oxidation catalyst to form the aromatic carboxylic acid and intermediates thereto. A product stream containing unreacted alkyl aromatic, the aromatic carboxylic acid product, any intermediates leading thereto formed in the oxidation reaction, and any products from undesirable side reactions in mother liquor solvent, is withdrawn through outlet pipe 24. The product stream is treated using conventional techniques to separate its components and to recover the aromatic carboxylic acid product.

A substantial portion of the heat generated in the exothermic reaction is removed from the reaction mixture by vaporization of the solvent and, to a smaller extent, of the alkyl aromatic. The vaporized material and any unreacted oxygen and other components of the air fed to the reactor 11 pass upward through the reactor 11 and are withdrawn from the reactor 11 from a point above the top level D of the liquid reaction mixture in the reactor 11, and passed to the overhead condenser system 18 where the vaporized solvent and alkyl aromatic are condensed for recycle to the reactor 11 in pipe 19. The non-condensible gases are vented from the condenser system 18 through the vent 25. The remainder of the heat generated results in an increase in the temperature of the reaction mixture and hence of the reaction temperature.

Suitable alkyl aromatics for use in the method of this invention include toluene, o-, m- and p-xylene, and the trimethylbenzenes, and the respective aromatic carboxylic acid products are benzoic acid, orthophthalic acid, isophthalic acid, terephthalic acid, and the tricarboxylic acids. In a preferred embodiment of the method of this invention, p-xylene is oxidized to terephthalic acid.

Suitable solvents for use in the method of this invention include any $C_2$–$C_6$ fatty acids such as acetic acid, propionic acid, n-butyric acid, isobutyric acid, n-valeric acid, trimethylacetic acid and caproic acid and water and mixtures thereof. Preferably, the solvent is a mixture of acetic acid and water, which more preferably contains from 0.5 to 20 weight percent of water, as introduced into the oxidation reactor.

The source of molecular oxygen for the oxidation of this invention can vary in molecular oxygen content from that of air to oxygen gas. Air and enriched air are the preferred sources of molecular oxygen. The oxygen-containing gas fed to the reactor should provide an exhaust gas-vapor mixture containing (measured on a solvent-free basis) of from 2 to 8 volume percent oxygen. For example, when each alkyl substituent on the aromatic ring of the alkyl aromatic is a methyl group, a feed rate of the oxygen-containing gas sufficient to provide oxygen in the amount of from 1.4 to 2.8 moles per methyl group will provide such 2 to 8 volume percent of oxygen (measured on a solvent-free basis) in the gas-vapor mixture in the condenser.

Suitable catalysts for use include any catalyst system conventionally used for liquid phase oxidations of alkyl aromatics and preferably include a mixture of forms of cobalt, manganese and bromine which are soluble in the solvent employed. When the catalyst comprises soluble forms of cobalt, manganese and bromine, cobalt (calculated as elemental cobalt) is present in the range of from about 0.1 to about 10.0 milligram atoms (mga) per gram mole of the alkyl aromatic; manganese (calculated as elemental manganese) is present in the ratio of from about 0.1 to about 10.0 mga per mga of cobalt (calculated as elemental cobalt); and bromine (calculated as the elemental bromine) is present in the ratio of from about 0.2 to about 1.5 mga per mga of total cobalt and manganese (both calculated as the elemental metals).

In the preferred embodiment of the method of this invention in which the catalyst employed comprises a mixture of soluble forms of cobalt, manganese and bromine, and the solvent is acetic acid or a mixture thereof with water, each of cobalt and manganese can be provided in any of its known acetic acid-soluble ionic or combined forms, for example, as cobalt and/or manganese carbonate, acetate tetrahydrate, and/or bromide. However, because of (1) the aforesaid requirement that the mga ratio of bromine (calculated as elemental bromine)-to-total cobalt and manganese (each calculated as the elemental metal) be 0.2 to 1.5 and (2) the fact that the bromides of cobalt and manganese have a bromide-to-metal gram atom ratio of 2:1, the catalysis can not be provided by use of bromides of both cobalt and manganese. Rather the catalysis can be provided by appropriate ratios of the bromide salts and other acetic acid soluble forms containing no bromine, for example, the acetates. As a practical matter the 0.1–10:1 manganese-to-cobalt mga ratio is provided by use of their acetic acid soluble forms other than bromides, for example, both as acetate tetrahydrates, and the 0.2–1.5:1.0 elemental bromine-to-total cobalt and manganese mga ratio is provided by a source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese mga ratio of 0.2–1.5:1.0. The bromine ion released from the organic bromides at the oxidation operating conditions can be readily determined by known analytical means. Tetrabromoethane, for example, at operating temperatures such as 170° to 225° C. has been found to yield about 3 effective gram atoms of bromine per gram mole.

The feed stream introduced into reactor 11 in FIG. 1 contains each of the alkyl aromatic and catalyst dissolved in solvent. Since heat generated in the highly exothermic liquid phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After removal of the aromatic polycarboxylic acid product from the product stream, at least a portion of the mother liquor (solvent) in the resulting product stream is generally recycled to the reactor, for example, in the feed stream. The weight ratio of the solvent in the feed stream-to-the total amount of solvent (including the amounts recycled from the condenser system and from the product system, as well as any make-up solvent) introduced into the reactor is in the range of from about 0.15:1 to about 0.4:1. Of course, the alkyl aromatic and catalyst could be introduced into the reactor separately from the solvent rather than dissolved in solvent in a feed stream as shown in FIG. 1. The weight ratio of the total amount of solvent introduced into the reactor-to-the total amount of alkyl aromatic introduced into the reactor is in the ranqe of from about 1:1, preferably from about 2:1, to about 10:1, preferably to about 6:1.

The weight ratio of solvent recycled to the reactor from the overhead condenser system-to-the solvent introduced into the feed stream, if used, is at least about 1.5, preferably at least about 2.5. More preferably, the weight ratio of solvent recycled to the reactor from the overhead condenser system-to-the solvent introduced in the feed stream, if used, is less than about 5.7, most preferably less than about 4.0.

In operation, the minimum pressure at which the reactor is maintained is that pressure which will maintain a substantial liquid phase of the alkyl aromatic and at least 70 percent of the solvent. The alkyl aromatic and solvent not in the liquid phase because of vaporization by heat of reaction, is withdrawn from the reactor and condensed, and the condensate is returned to the reactor as the recycle solvent. When the solvent is an acetic acid-water mixture, suitable reaction gauge pressures are in the range of from about 0 kg/cm$^2$ to about 35 kg/cm$^2$, and typically are in the range of from about 10 kg/cm$^2$ to about 30 kg/cm$^2$.

The process temperature employed should, on the one hand, be so low that the oxidation occurs with a particularly low amount of losses, but, on the other hand, be so high that a sufficient conversion of the alkyl aromatic is attained. Process temperatures suitable for use in the method of this invention generally range from about 120° C., preferably from about 150° C., to about 240° C., preferably to about 230° C. Within these broad ranges, various narrower ranges are generally preferred depending on the particular alkyl aromatic being oxidized. For example, when the alkyl aromatic is p-xylene, the preferred overall temperature range within the reactor is from about 175° C. to about 225° C.

The residence time in the reactor is determined as the quotient obtained by dividing the liquid volume in the reactor by the throughflow quantity. The fractional volume occupied by gas and vapor must be taken into account in calculating the liquid volume. Typically in commercial operations, the residence time in the reactor is in the range of from about 20 to about 90 minutes.

The present invention will be more clearly understood from the following examples.

EXAMPLES 1-4

Examples 1-4 involve four oxidation runs in a commercial unit for the conversion of p-xylene to terephthalic acid. The reactor was equipped with an overhead condenser system for condensation of the solvent and p-xylene which vaporized in the reactor during the exothermic liquid phase oxidation and also for return of the condensed material to the reaction mixture in the reactor by gravity flow. In each of Examples 1 and 3, the aforesaid condensed materials were recycled to the reactor at a point near the top thereof; while in each of Examples 2 and 4, approximately 20 percent of the aforesaid condensed materials was recycled to the reactor at a point near the bottom thereof, and the remainder of the condensed materials was recycled to the reactor at a point near the top thereof.

Except as indicated hereinbelow, each of Examples 1-4 was performed at a temperature in the range of from about 150° C. to about 230° C. and at an absolute gauge pressure in the range of from about 10 kg/cm$^2$ to about 30 kg/cm$^2$ and with a mixture of acetic acid and water containing from about 10 to about 20 weight percent of water as the solvent. In each example, the catalyst comprised cobalt, manganese and bromine components which were in the form of soluble $Co(C_2H_3O_2)_2.4H_2O$, $Mn(C_2H_3O_2)_2.4H_2O$ and hydrobromic acid, respectively. The cobalt component, calculated as elemental cobalt, was present in the solvent in the reactor at a level of from about 0.5 to about 2.0 mga per gram mole of p-xylene. The ratio of the number of gram atoms of the manganese component, calculated as elemental manganese, per gram atom of the cobalt component, calculated as elemental cobalt, was in the range of 1:1 to 6:1, and the ratio of the number of gram atoms of the bromine component, calculated as elemental bromine, per gram atom of the combined cobalt and manganese components, calculated as elemental cobalt and elemental manganese, was 0.25:1 to 1:1. Solvent residence times in the oxidations of Examples 1-4 were between 40 and 90 minutes. In each oxidation, the oxygen concentration (measured on a solvent-free basis) in the gas-vapor mixture in the condenser was between 0.5 and 5 mole percent.

In Examples 1 and 2, with the rates of introduction of p-xylene to the reactor being the same and each being in the range of from about 100 to about 300 kilograms per minute in each example, the minimum reaction temperature that could be used in Example 2 before the pressure drop in the condenser system exceeded the available elevation head was approximately 20° C. lower than the corresponding minimum temperature that could be employed in Example 1.

In Examples 3 and 4, with the reaction temperatures being the same and terephthalic acid of the same quality and with the same selectivity and product quality (as measured by the concentrations of toluic acid and 4-carboxybenzaldehyde) being produced in each example, the maximum rate of introduction of p-xylene that could be used in Example 4 before the pressure head in the condenser system exceeded the available elevation head was approximately 43 percent higher than the corresponding maximum rate of introduction of p-xylene that could be used in Example 4.

From the above description, it is apparent that the objects of this invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. In a method for the continuous production of an aromatic carboxylic acid by the liquid phase, exothermic oxidation of an alkyl aromatic with an oxygen-containing gas in a solvent in an oxidation reactor at an elevated temperature and pressure and in the presence of an oxidation catalyst, wherein heat generated in the oxidation reactor is at least partially dissipated by vaporization of the solvent therein, the vaporized solvent is withdrawn from the top of the oxidation reactor and condensed in an overhead condenser system and the condensed solvent is recycled by gravity flow to the oxidation reactor, the improvement comprising recycling at least a portion of the condensed solvent from the overhead condenser system to the bottom portion of the oxidation reactor through a line exterior to the oxidation reactor, to maximize the available pressure head between the overhead condenser and the point in the reactor to which the aforesaid portion of the condensed solvent is recycled.

2. The method of claim 1 wherein the aromatic carboxylic acid is terephthalic acid which is produced by the liquid phase oxidation of p-xylene.

3. The method of claim 1 wherein the oxidation catalyst comprises cobalt, manganese and bromine components.

4. The method of claim 1 wherein the solvent comprises a mixture of acetic acid and water containing from about 0.5 to about 20 weight percent of water.

5. The method of claim 1 wherein the temperature in the reactor is in the range of from about 120° C. to about 230° C.

6. The method of claim 1 wherein the absolute pressure in the reactor is in the range of from about 0 to about 35 kg/cm$^2$.

* * * * *